US 6,585,707 B2

(12) United States Patent
Cabiri et al.

(10) Patent No.: US 6,585,707 B2
(45) Date of Patent: *Jul. 1, 2003

(54) DRUG DELIVERY DEVICE HAVING IMPROVED ADHESION AND ATTACHMENT SYSTEM FOR DRUG DELIVERY DEVICE

(75) Inventors: Oz Cabiri, Maccabim (IL); David Katz, Mashav Mazor (IL); Mario Rozanowich, Moshav Cafri Ezer (IL); Haim Danon, Kirvat Ono (IL); Joseph Gross, Mashav Mazor (IL); Izrail Tsals, Sudbury, MA (US); Craig Brodeur, Marlborough, MA (US); Robert Etheredge, Natick, MA (US)

(73) Assignee: Elan Pharma International Limited, Shannon (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/315,629

(22) Filed: May 20, 1999

(65) Prior Publication Data

US 2001/0056262 A1 Dec. 27, 2001

Related U.S. Application Data

(60) Provisional application No. 60/086,207, filed on May 21, 1998.

(51) Int. Cl.[7] ................................................. A61F 13/02
(52) U.S. Cl. .................................... 604/307; 602/57
(58) Field of Search ................................ 604/174, 180, 604/513, 41, 151, 93, 304–308, 386–387; 602/41, 53, 58, 52, 54–57; 128/DIG. 26

(56) References Cited

U.S. PATENT DOCUMENTS

| 4,336,806 | A |   | 6/1982  | Eldridge, Jr. |           |
|-----------|---|---|---------|---------------|-----------|
| 4,397,647 | A | * | 8/1983  | Gordon        | 604/180   |
| 4,666,441 | A | * | 5/1987  | Andriola et al. | 604/304 |
| 4,690,680 | A | * | 9/1987  | Higgins       | 604/386   |
| 4,839,206 | A | * | 6/1989  | Waldenberger  | 428/41.5  |
| 4,844,061 | A | * | 7/1989  | Carroll       | 128/207.17|
| 5,064,422 | A | * | 11/1991 | Wick          | 604/307   |
| 5,086,763 | A | * | 2/1992  | Hathman       | 602/42    |
| 5,137,520 | A | * | 8/1992  | Maxson et al. | 604/180   |
| 5,192,274 | A | * | 3/1993  | Bierman       | 604/180   |
| 5,308,887 | A | * | 5/1994  | Ko et al.     | 522/148   |
| 5,395,344 | A | * | 3/1995  | Beisang, III et al. | 604/180 |
| 5,449,340 | A |   | 9/1995  | Tollini       |           |

(List continued on next page.)

FOREIGN PATENT DOCUMENTS

| DE | 3140192 A1 | 4/1983 | ........... A61M/25/02 |
| EP | 0247571    | 2/1987 | ........... A61M/25/02 |
| EP | 0409583 A2 | 1/1991 | ........... A61M/25/02 |
| EP | 0689853 A2 | 3/1996 | ........... A61N/25/02 |
| WO | WO 96/37244 | * 11/1996 | |

Primary Examiner—Brian L. Casler
Assistant Examiner—Michael M Thompson
(74) Attorney, Agent, or Firm—Caesar, Rivise, Bernstein, Cohen & Pokotilow, Ltd.

(57) ABSTRACT

A system adapted to be disposed between a rigid or semi-rigid device and human skin for reliably attaching the device to the skin for an extended period of time. The system includes a skin-contacting surface for adhering to human skin, and an opposed surface for attachment to a rigid or semi-rigid device. The system is attached along its opposed surface to a portion of the total area of the adjacent surface of the device. When the device is subjected to external stress, the stress is transmitted through the area of attachment and distributed to the unattached area. This minimises stress on the skin and reduces the chance of detachment from the skin.

16 Claims, 5 Drawing Sheets

U.S. PATENT DOCUMENTS

| | | | |
|---|---|---|---|
| 5,589,122 A | * 12/1996 | Leonard et al. | 264/146 |
| 5,599,602 A | * 2/1997 | Leonard et al. | 428/56 |
| 5,660,922 A | * 8/1997 | Herridge et al. | 428/214 |
| 5,693,032 A | 12/1997 | Bierman | |
| 5,756,117 A | * 5/1998 | D'Angelo et al. | 424/449 |
| 6,010,527 A | * 1/2000 | Augustine et al. | 602/14 |

* cited by examiner

DRUG DELIVERY DEVICE HAVING IMPROVED ADHESION AND ATTACHMENT SYSTEM FOR DRUG DELIVERY DEVICE

This application claims the benefit of provisional application No. 60/086,207, filed May, 21, 1998.

TECHNICAL FIELD

This invention relates generally to systems for attaching rigid or semi-rigid structures to human skin, and in particular to medical devices for attachment to the skin of the human body.

BACKGROUND OF THE INVENTION

There are certain types of ambulatory medical devices such as miniature infusion pumps, iontophoretic devices and the like that are designed to be attached to human skin during use. Due to the nature of these devices many are rigid and attachment to the skin for a prolonged period of time has been unsuccessful. It is difficult to successfully adhere a rigid device to the skin surface for a prolonged period of time due to the rigidity of the device, the geightened center of gravity above the adhesion level, and the flexibility and pliability of the skin.

Rigid devices of the type disclosed in WO 97/10012 are presently applied to the skin by means of pressure sensitive adhesive. These devices show signs of failure within 24 hours of attachment and have completely detached before 48 hours have elapsed from the time of application. Such devices will be collectively referred to herein as rigid devices, except where otherwise specified.

Commercially available bandages or skin adhering tape employ the same types of pressure sensitive adhesive and reliably adhere to the skin for long periods of time, for example for one or more week(s). Conventional pressure sensitive adhesives consist generally of silicone, butyl or acrylic components that are formulated in such a way so that reliably adhere to the skin.

Bandages or skin adhering tape and present attachment means for rigid devices to the skin is that the adhesive system extends the adhesive to the edge of the device which is adhered to the skin.

It is at the interface between the rigid device and the skin that challenges adhesion, particularly in the case of rigid devices, and causes system failure.

The detachment of rigid devices from the skin typically occurs when there is a failure in the underlying skin integrity leading to separation of the device along with the outer skin layers. Reactions to external stress are responsible for most device to skin adhesion failures. In this regard, the areas of skin of greatest concern are the outermost layers of the epidermis, more particularly the stratum corneum. In this region of the skin there are multiple cell layers (as many as 150) which are held together or bonded by nodes known as desmosomes resulting in a flexible three-dimensional web. Although usually viewed as dead skin cells, the stratum corneum is, in fact a dynamic functional portion of the epidermis that provides protection for the lower skin layers. The structure of the stratum corneum is very compliant and has the ability to easily relieve stress applied thereto, thereby avoiding disruption of lower layers and maintaining the integrity thereof. When the skin is stressed, deep skin fracture is prevented because of the rupture of desmosome bonds through fatigue resulting in relief of stress through sloughing of surface layers of skin cells.

Skin is almost unmatched in its compliance and ability to relieve stresses. In particular, skin is about forty times more compliant than any commercially available pressure sensitive adhesive. Even the most compliant vinyl carrier for an adhesive will be about one hundred and thirty times less compliant than skin. A moulded plastics part of the type represented by a rigid device does not provide any compliance and would be close to zero on a relative compliance scale. Anything attached to the stratum corneum applies a stress to the skin. Thus, because of the difference in compliance between a rigid device and the skin there will always be a shear force between the skin and an adhesive system used to adhere said device to the skin. As indicated above, the skin relieves any stress by shearing.

Presently, rigid medical devices are completely attached along the lower surface to the skin by means of adhesive. The resultant rigid attachment maximises the stress potential on the skin leading to early signs of detachment and often complete detachment prior to the completion of the treatment provided by the device.

In addition, medical devices that infuse drug into a patient typically require the drug to travel from a container distal to the point of infusion. This results in a drug temperature change or flux that may be harmful to the efficacy of the drug and patient.

Accordingly, there is a need for a skin adhesive system that will adhere a rigid device to the skin for extended periods of time for use in effective therapy and diagnosis, as the case may be. Any such device should provide for both secure attachment and easy removal of the device. Additionally, effective adhesive systems for use in connection with infusion systems minimize the temperature flux of the drug which may optimize efficacy and overall patient benefit.

SUMMARY OF INVENTION

The present invention provides a system adapted to be disposed between a rigid or semi-rigid device and human skin for reliably attaching the device to the skin for an extended period of time, the system having a skin-contacting surface for adhering to the skin and an opposed surface, for attachment to the device over a portion of the total area of the adjacent surface of the device thereby minimising stress on the skin and reducing the tendency of the device to detach from the skin.

The system transmits any external stress to which the device is subjected and distributes it to the unattached areas of skin proximate to the adjacent surface of the device.

The system according to the invention provides for secure skin attachment for extended periods of time and easy removal of the device, when required. The system provides for superior performance relative to known systems and in tests has shown suitability for application to multiple sites and three-day operation or longer. In particular, the system according to the invention has been shown to be effective for more than 72 hours of secure device attachment to the skin while allowing the wearer to undergo the normal activities of daily life.

The system according to the invention by virtue of its construction provides sufficient relaxation of any stress before transition thereof to the skin. It will be appreciated that the lower the magnitude of any stress imparted to the skin, the better.

In one embodiment, the system comprises a structure which is a laminar element.

Preferably, the system extends beyond the adjacent surface of the device.

An important aspect of the present invention is that it minimises the forces on the interface between the device and the skin at the edge of the adhesive. This area must be the most compliant area of the system.

Thus, preferably each area attached to the skin is located towards the centre of the system so as to allow for flexibility towards the periphery thereof.

Further, preferably, the skin contacting surface comprises a pressure sensitive adhesive.

Still further, preferably, the system comprises a carrier element having viscoelastic properties approaching those of skin.

The carrier must be made of a compliant material or otherwise be capable of even distribution of stress, more especially a material that minimises local stress on the skin when a stress is applied to the device.

In a preferred embodiment, the system is attached to the adjacent surface of the device at a number of discrete areas.

Typically, three discrete areas or anchor points will be used.

Suitably, the areas of attachment to the device are arranged at the apices of a triangular area or other regular pattern or shape.

Thus, the structure is attached to the device over a limited area leaving the rest of said structure to move freely with the skin. This creates a flexible 'skirt' around each discrete attached area. Maximisation of the flexible area in the system according to the invention is a key component in the adhesion longevity achieved.

Extended wear time with the system according to the invention is accomplished by minimising the stresses imparted to the skin that cause local skin fatigue failure and eventual detachment of the device. The construction embodied in the system according to the present invention allows the skin to move more freely than in the case of prior art systems, thereby reducing the magnitude of any stresses on the skin.

The system can be permanently attached to the device at each area of attachment.

Alternatively, the system is detachable from the device.

This feature allows the device to be replaced without detaching the skin-contacting surface from the skin.

The system according to the invention can be used with any product that has a rigid or semi-rigid construction and has to be attached to the human body. Such devices include: infusion systems of the type covered by International Publication No. WO 97/10012; iontophoretic drug delivery systems; minimally invasive sensors, including glucose sensors; diagnostic devices such as devices used in heart rate, pulse and ECG monitoring; ostomy products; nerve stimulators; external programming, data collection and monitoring devices for pace makers and defibrillators; implantable hearing aids and the like.

In one embodiment, the system is attached to the device by means of the co-operating elements of a fastening system located on the base of the device and the opposed face of the system, respectively.

Adhesive attachment of the system to the device can be achieved by means of a locally applied adhesive such as a pressure sensitive, epoxy or heat or UV-activated adhesive.

In a further embodiment, the device is provided with a relief cavity which can accommodate deflection of the skin in use which would otherwise result in higher stress and a detachment thereof.

Thus, the base of the device can be contoured to allow a maximum flexibility in relation to the skin. For example, the base of the device can be designed with a concave or relieved area. This creates an area for skin to flex into during physical activity without it pressing against the device and thus increasing stress on the skin.

The relief cavity can be a concave area in the base of said device.

The device to be applied to the skin may be provided with an integral needle for delivery of a substance through the skin.

With such devices, a flexible area is preferably provided at the locus where the needle penetrates the structure for access to the skin.

The area where the needle penetrates the skin is also an adhesive edge and adhesion longevity is improved by creating a flexible skirt around the hole resulting from or allowing for the needle penetration. This flexible skirt would typically extend 1–2 mm radially from the adhesive edge. This skirt allows for stress relief when the needle moves in relation to the skin.

By providing a flat section around the area where the needle penetrates the system concentrates pressure against the skin during application. This allows maximum wetting of the skin surface by the adhesive to ensure effective device operation.

Also suitably the system is provided with a 2–3 mm diameter hole through which the needle penetrates.

A 2–3 mm diameter hole in the skin adhesive allows the device needle to the inserted into the skin without having to pass through the adhesive layer. The small size of the hole is necessary so that the skin remains taut to ensure penetration thereof by the needle.

Preferably, one area of attachment is provided with an extension to the periphery of the system which facilitates removal of the device when required.

In a further aspect of the invention there is provided a method for reliably attaching a rigid or semi-rigid device to human skin for extended period of time, comprising the steps of:

providing a system having a skin-contacting surface for adhering to human skin and an opposed surface for attachment to a rigid or semi-rigid device;

attaching the opposed surface to a portion of the total area of the adjacent surface of the rigid or semi-rigid device; and attaching the skin-contacting surface to the skin, whereby when the device is subject to external stress, thereby minimising stress on the skin and reducing the chance that the device will detach from the skin.

Other objects, features and advantages of the present invention will become apparent upon reading the following detailed description of the embodiments of the invention, when taken in conjunction with the drawings and appended claims.

BRIEF DESCRIPTION OF THE DRAWINGS

The invention will be further illustrated by the following description of embodiments thereof given by way of example only with reference to the accompanying drawings in which.

DETAILED DESCRIPTION OF THE INVENTION

Figure 1:
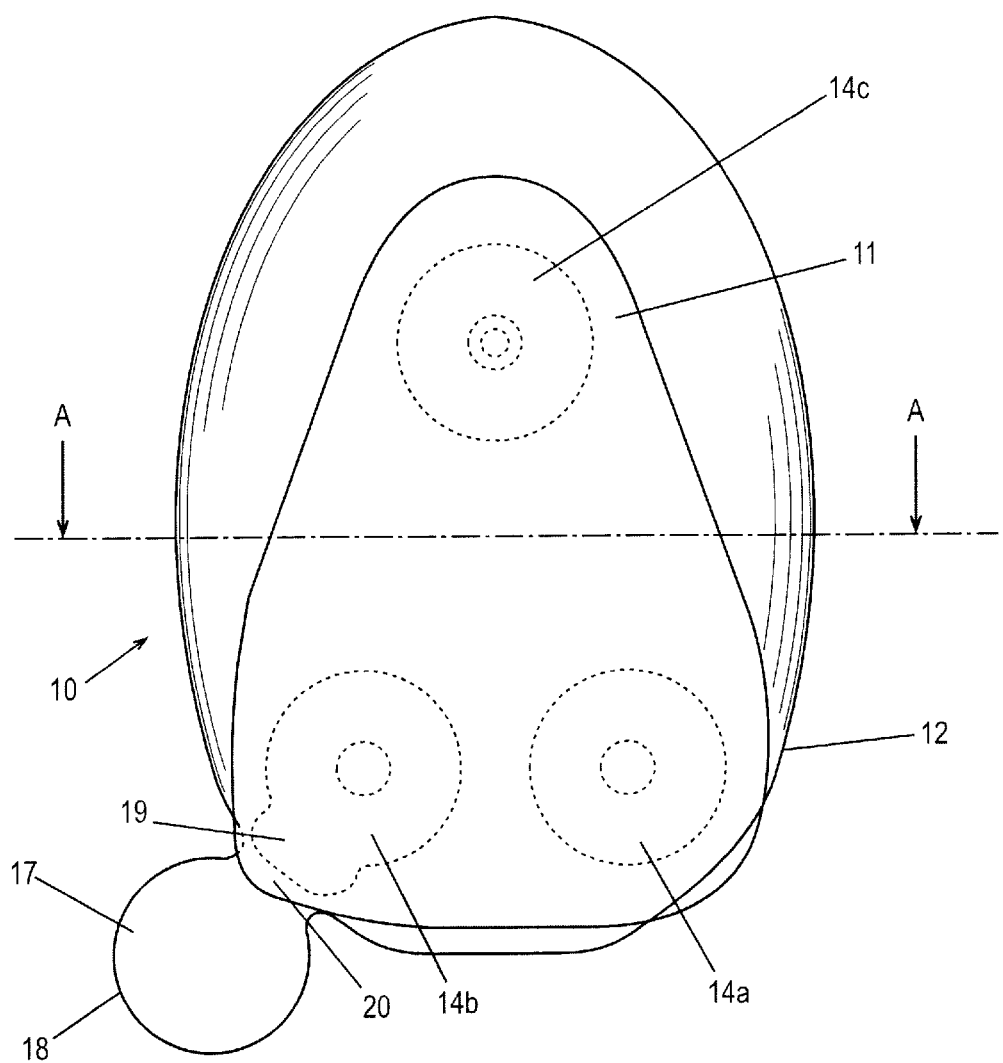
FIG. 1 is a plan view of a preferred embodiment of the system according to the invention.
Figure 1A:
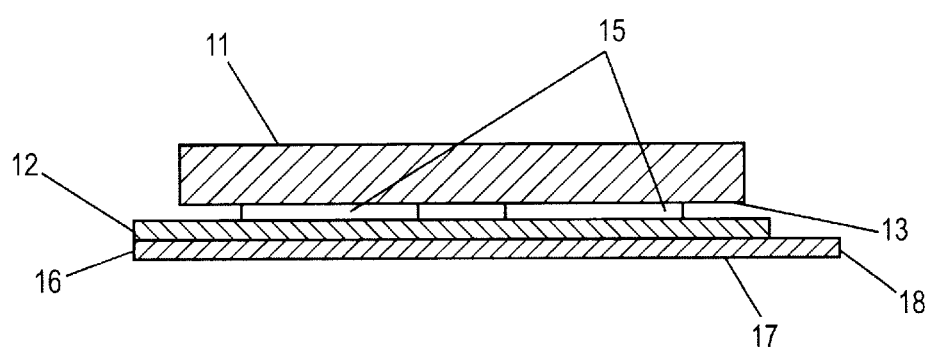
FIG. 1A is a cross-sectional view of the preferred embodiment of FIG. 1.

Referring to FIG. 1 of the drawings there is indicated, generally at 10, part of a system according to invention which enables a rigid or semi-rigid device 11 to be reliably attached to the skin of a human body for an extended period of time. The system as shown in FIG. 1A includes a structure, indicated generally at 12, which is disposed in the interface between the device 11 and the skin (not shown). The device has a base 13 and is attached to the structure 12 on its upper surface opposed to the base of the device at three areas 14a, 14b and 14c by means of adhesive 15. The structure 12 has a skin-contacting surface 16, which is adhered to the skin in use by means of a pressure-sensitive adhesive.

Such pressure sensitive adhesives include acrylic, butyl, hydrogel, polyisobutylene, silicone and the like adhesives. Adhesives will suitably be the same as those used in commercially available bandages and sticking plasters. However, Avery Fastape, a double sided polyester film tape is preferred. Moreover, the thickness of the adhesive should be between 1.5 and 2.0 mils.

The skin-contacting surface 16 is covered with a conventional release liner 17 prior to use. The release liner 17 is removed by means of a tab 18.

The release liner can be composed of a variety of materials due to the cancelled adhesive area which will typically be a feature of the system according to the invention. Standard release liners made of low cost siliconised paper or plastic film can be employed. If the cancelled area is not present a more expensive flourosilicone-coated premium release liner or centre butterfly tab would be required to avoid tearing the liner or damage to the adhesive attachment.

The system per se can be a layer of a polymeric material with the requisite properties and having a skin-contacting surface.

Alternatively, the laminar element can be a layer of double-sided adhesive material of sufficient rigidity.

As shown in FIG. 1, attachment area 14b has an extension 19 which terminates just short of edge 20 of the structure 12. This feature serves to aid removal of the device 11 from the skin (not shown) when required, because failure of the adhesive tends to occur at this point. Positioning the extension 19 near the liner removal tab 18 allows for easy removal of the liner 17 also.

By locating the area of attachment close to the edge of the skin-contacting surface, removal forces are lowered. This occurs because the area of attachment is cancelled at this point and a mechanical advantage can be obtained for peeling off the device. The result is a localised adhesion force reduction over time that allows the edge of the adhesive to lift. The user can take advantage of this and start the removal process by peeling off the device from this point. Positioning this 'cancelled area' near the removal tab, which will be provided on the release liner, allows for easy removal of the liner also.

Figure 2A:
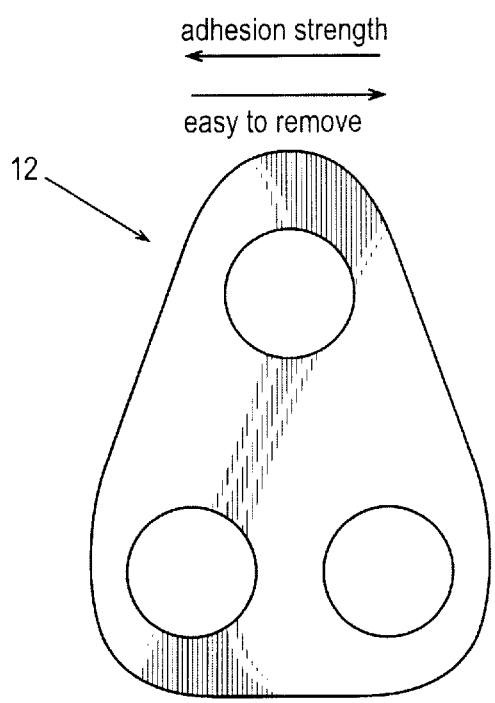
FIGS. 2A–C are schematic representations of various discrete areas of attachment employed in the system according to the invention with an indication of adhesion strength versus ease of removal for the respective variations.
Figure 2B:
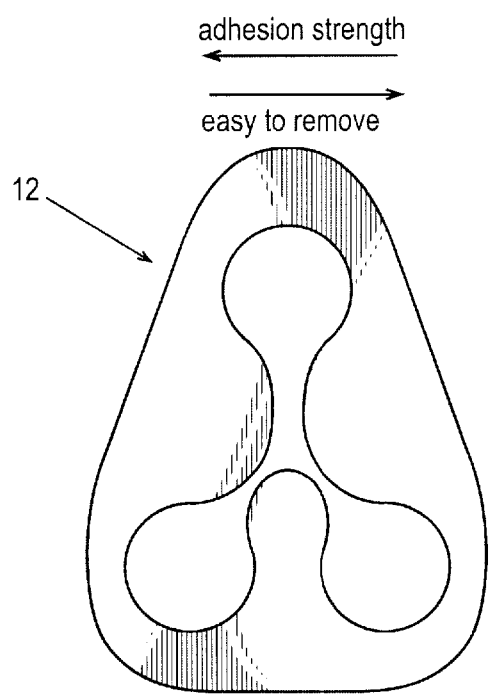
Figure 2C:
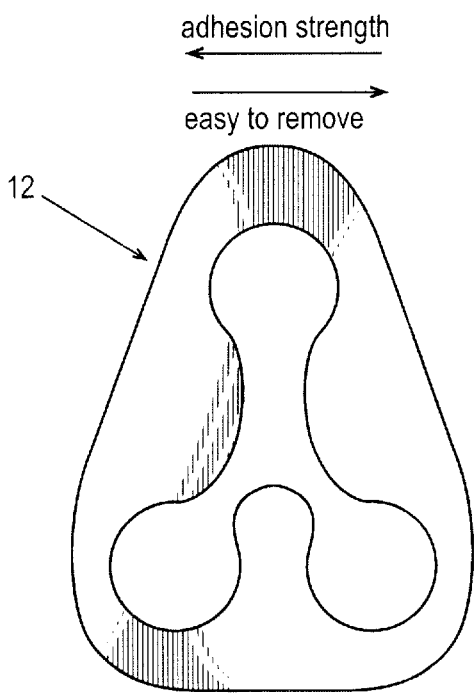

Referring to FIGS. 2A–2C there are depicted three variations of the discrete area or areas of attachment employed in a system of the type depicted in FIG. 1.

FIG. 2A corresponds to the system used in FIG. 1 and FIGS. 2B and 2C represent situations where the three areas of FIG. 2A are joined by areas of adhesive.

As indicated by the labelled arrows, the smaller the area of the structure 12 attached to the device 11, the greater the adhesive strength of the system and the more difficult it is to remove the device from the skin and vice versa.

It will be appreciated that the greater the area that is rigidly connected to the device, the larger the magnitude of the stress that can be imparted to the skin causing a reduction in adhesion force over time and facilitating removal. Adhesion life and ease of removal are inversely related. Thus, by connecting the adhesion points or enlarging them, one facilitates ease of removal of the device, when required.

Figure 3:
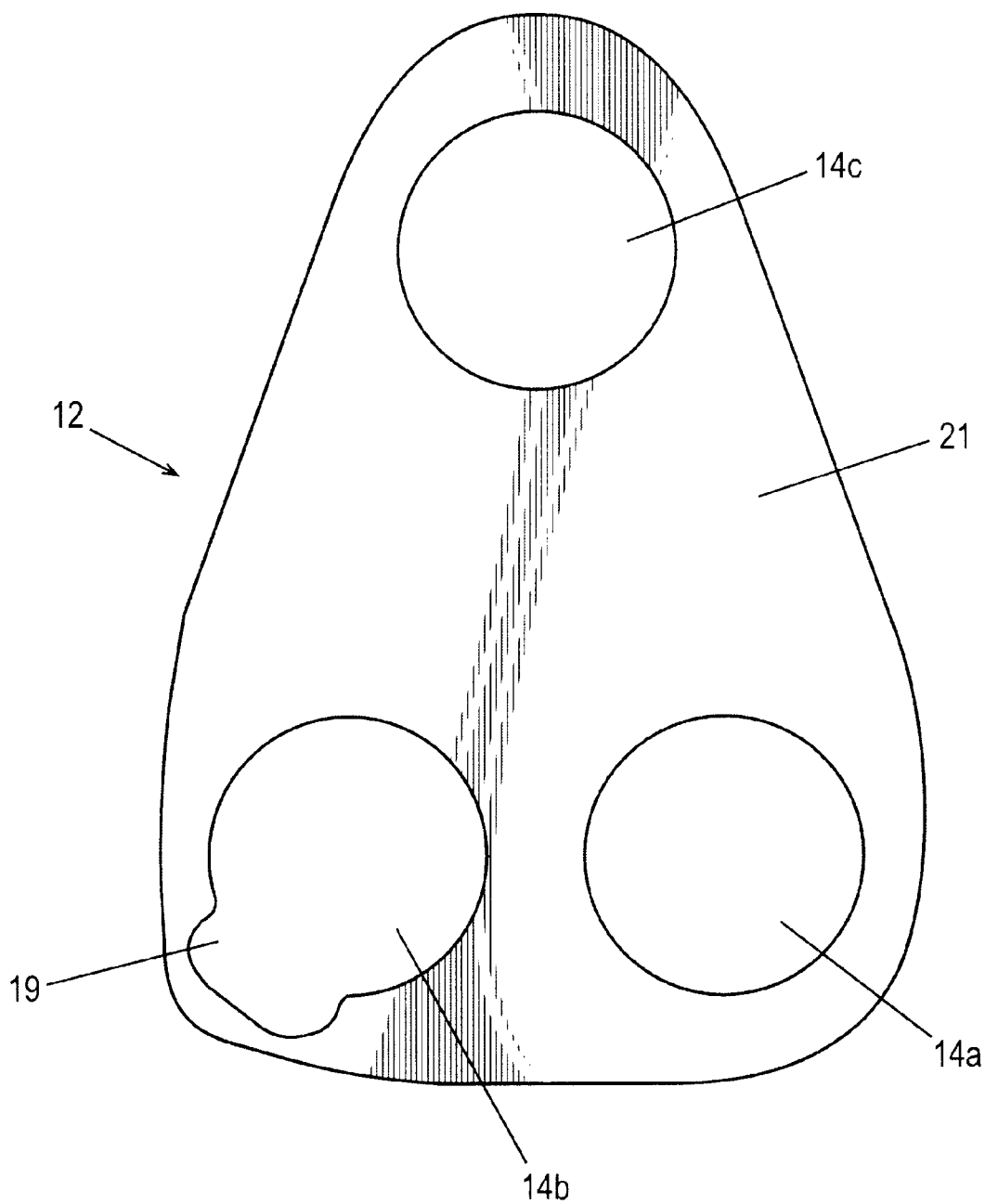
FIG. 3 is a top view of the system according to the invention showing discrete areas of attachment and a local failure point.

Referring to FIG. 3, there is indicated part of the structure 12 depicted schematically in FIG. 1 viewed from above showing the areas of attachment 14a–14c disposed on surface 21 of the structure 12 to which the device is attached. The arrangement of the extension 19 of the attachment area 14b stopping just short of the edge of the surface 21 creates a local failure point which facilitates removal of the device 11 when required.

FIGS. 4a–e show various options for attaching the structure 12 used in the system 10 according to the invention to the device 11. In FIGS. 4a–e, the same reference numerals are used to depict the same parts.

Figure 4A:
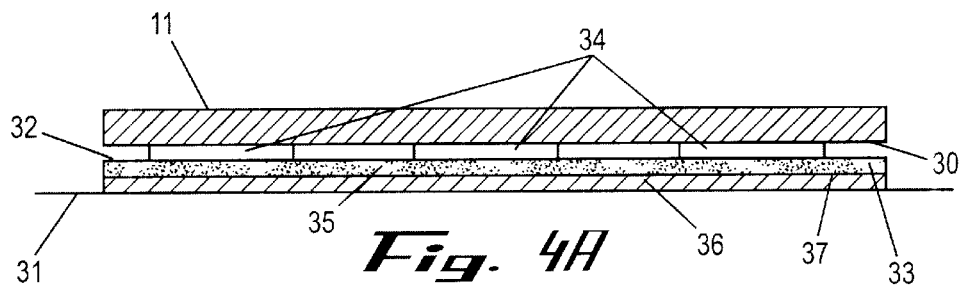
FIGS. 4a–e are cross-sectional views depicting various options for attachment of the system according to the invention to a rigid or semi-rigid device.

In FIG. 4A there is shown base 30 of the device 11 to be secured to skin 31 of a human being using the system 10 according to the invention. Base 30 is attached to surface 32 of a structure 33 at three areas 34 of adhesive. The structure 33 is comprised of a carrier element 35 having viscoelastic properties approaching that of skin provided with a layer of pressure sensitive adhesive 36 on its skin-contacting surface 37.

The carrier element, when such is present, can be formed from foams, especially flexible foams manufactured by Kendall Polychem or and Avery Dennison. In particular, the preferred foams included Actiflex(made by Kendall Polychem and PVC1, a PVC closed cell foam made by Avery Dennison under the model number Q527297, or be made of woven and non-woven fabrics. A suitable non-woven fabric is a spun-laced polyester marketed by Du Pont under the mark Sontara.

Figure 4B:
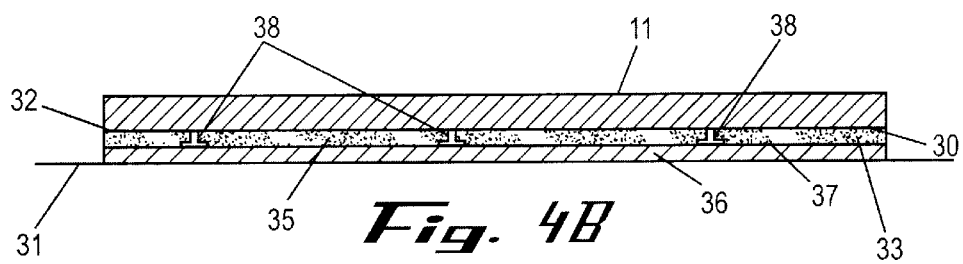

In FIG. 4B, the device is attached to the structure 33 by means of rivets 38 which extend through the structure.

Figure 4C:
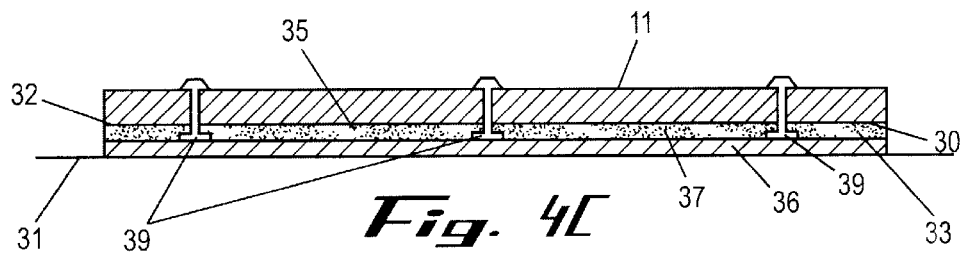

In FIG. 4C, the device 11 is attached to the structure 33 by means of a one-way snap attachment 39. In this embodiment, the device 11 is not removable from the structure 33.

Figure 4D:
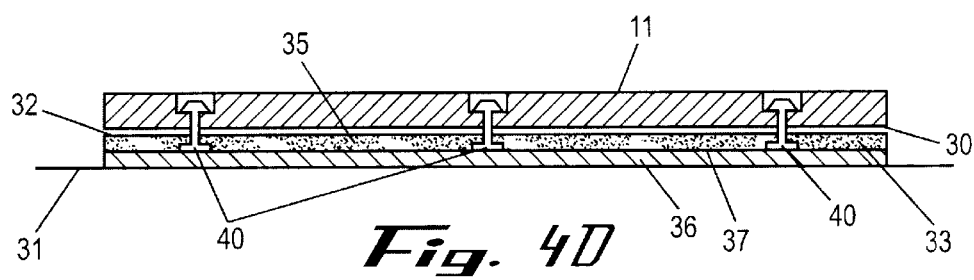

In FIG. 4D, the device 11 is attached to the structure 33 by means of a removable snap attachment 40.

Figure 4E:
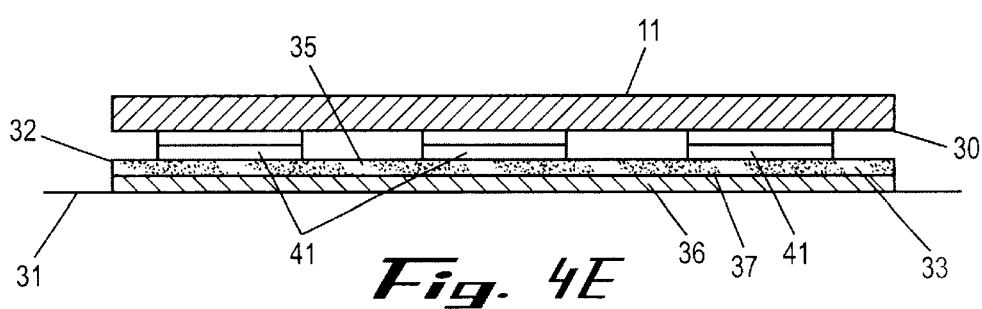

In FIG. 4E, the device is attached to the structure 33 by means of a hook and loop attachment means 41.

In the case of the embodiments depicted in FIGS. 4D and 4E the device is detachable from the structure 33, so that the structure can be left in contact with the skin and a further device attached thereto, if required.

Alternatively, attachment of the system to the device can be achieved by means of rivets, snaps, including mechanical snaps, heat, including posts for heat staking, or sonic welding, spring clips, hook and loop fasteners such as VELCRO® and magnetic fastening means or a combination thereof.

Figure 5:
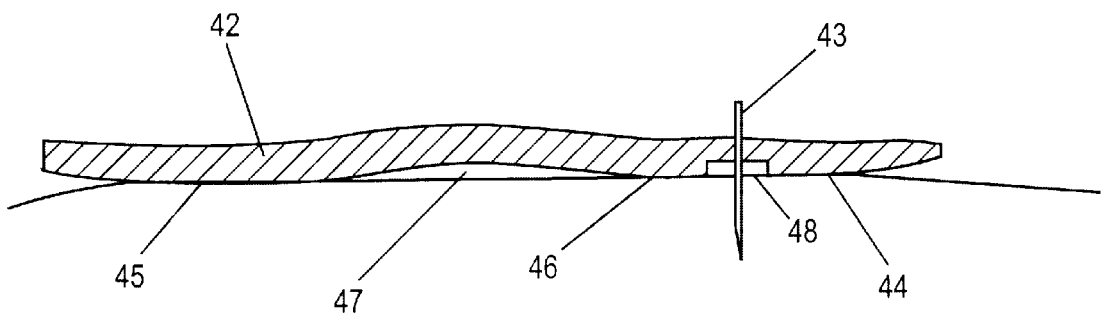
FIG. 5 is a cross-sectional schematic representation of the base and needle of a device as attached to the skin using a system according to the invention.

FIG. 5 illustrates a typical cross-sectional view of a medical device 42, with an integral needle 43, attached to a structure 44 at areas 45 and 46. Structure 44 is free to move where the device 42 is not attached to the structure 44 (indicated at 47). There is also an unattached area 48 of structure 44 immediately surrounding the needle 41. The area 47 where the structure 44 is unattached can accommodate deflection of skin in use and relieve stress. Because drug is delivered through the needle and the drug reservoir is effectively held proximate to the skin surface, the drug temperature will not change considerably prior to or during delivery. This is advantageous where drug temperature is sensitive and may change efficacy as temperature fluctuates. By maintaining a constant temperature, the drug is most effective and most beneficial to the patient.

Figure 6:
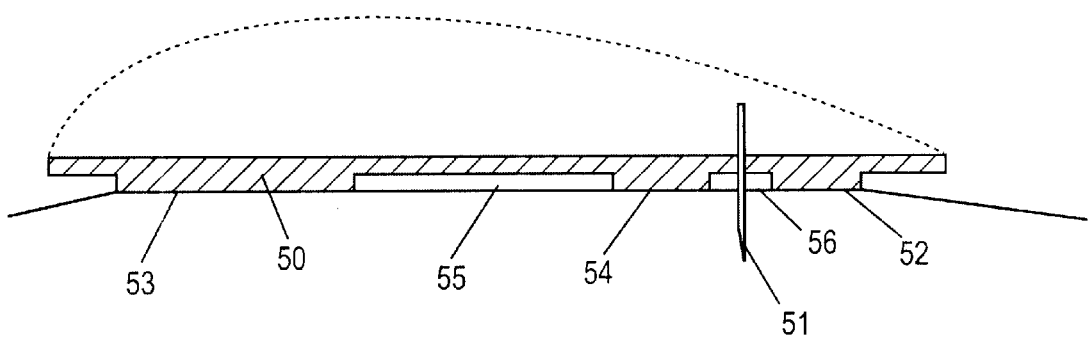
FIG. 6 is a further cross-sectional schematic representation of the base and needle of a device as attached to the skin using a system according to the invention.

FIG. 6 illustrates a further cross-section portion of a base 50 (shown in phantom) with an integral needle 51, attached to a structure 52 at areas 53 and 54. The structure 52 is free to move where the base 50 is not attached to the structure 52 shown at 55. There is also an unattached area 56 immediately surrounding the needle 51. The area 55 can accommodate deflection of skin in use and relieve stress.

It will be appreciated that the embodiments discussed above are preferred embodiments, and that various alternative embodiments are contemplated, falling within the scope of the appended claims.

What is claimed is:

1. An attachment system for reliably attaching a device to the skin of a being and wherein the device includes a rigid or semi-rigid base having a periphery, said system comprising:

a structure having a skin-attaching surface and a base-attaching surface, said skin-attaching surface comprising an adhesive for adhering to the skin of the being, said skin-attaching surface having a periphery larger than the periphery of said rigid or semi-rigid base; and said base-attaching surface having a central region and a peripheral edge and wherein said base-attaching surface is coupled to said rigid or semi-rigid base at discrete adhesive locations but is uncoupled to said rigid or semi-rigid base at its central region and at its peripheral edge, thereby minimizing stress omnidirectionally on the skin of the being and reducing the chance of premature detachment from the skin of the being.

2. The attachment system according to claim 1, wherein one portion of said peripheral edge is coupled to said rigid or semi-rigid base by adhesive.

3. The attachment system according claim 2, wherein said one portion forms an extension of one said discrete adhesive locations.

4. The attachment system of claim 1, wherein said structure forms a flexible skirt around each of said discrete adhesive locations.

5. The attachment system according to claim 1, wherein said skin-attaching-surface comprises a pressure sensitive adhesive.

6. The attachment system according to claim 1, wherein said structure comprises a carrier element having viscoelastic properties approaching those of skin.

7. The attachment system according to claim 1, wherein said discrete adhesive locations are arranged at the apices of a triangle.

8. An attachment system for reliably attaching a device to the skin of a being, and wherein the device includes a rigid or semi-rigid base having a first plurality of attachment members located thereon and a periphery, said system comprising:

a structure having a skin-attaching surface and a base-attaching surface, said skin-attaching surface comprising an adhesive for adhering to the skin of the being, said skin-attaching surface having a periphery larger than the periphery of said rigid or semi-rigid base; and said base-attaching surface being located opposite to said skin-attaching surface and comprising a central region, a peripheral edge and a second plurality of attachment members and wherein said first and second plurality of attachment members cooperate to couple said rigid or semi-rigid base to said base-attaching surface but wherein said central region and said peripheral edge remain uncoupled to said rigid or semi-rigid base, thereby minimizing stress omnidirectionally on the skin of the being and reducing the chance of premature detachment from the skin of the being.

9. An attachment system for reliably attaching a device to the skin of a being and wherein the device includes a rigid or semi-rigid base having a periphery, said attachment system comprising:

a structure having a skin-attaching surface and a base-attaching surface, said skin-attaching surface comprising an adhesive for adhering to the skin of the being, said skin-attaching surface having a periphery larger than the periphery of said rigid or semi-rigid base;

said base-attaching surface having a central region and a peripheral edge and wherein said base-attaching surface is coupled to said rigid or semi-rigid base at discrete adhesive locations but is uncoupled to said rigid or semi-rigid base at its central region and at its peripheral edge, thereby minimizing stress omnidirectionally on the skin of the being and reducing the chance of premature detachment from the skin of the being; and wherein a relief cavity is formed between the base and said structure which can accommodate deflection of the skin of the being in use which would otherwise result in higher stress and potential premature detachment thereof.

10. The attachment system according to claim 9 being adapted to permit the passage of a needle therethrough for delivery of a substance through the skin.

11. The attachment system according to claim 10 wherein said structure comprises a locus for permitting the needle access to the skin and wherein a flexible area is provided at the locus.

12. The attachment system according to claim 9, wherein one portion of said peripheral edge is coupled to said rigid or semi-rigid base by adhesive to facilitate removal of the base when required.

13. An attachment system for reliably attaching a device to the skin of a being, and wherein the device includes a rigid or semi-rigid base having a periphery, said system comprising:

a generally planar member having a skin-attaching surface and a base-attaching surface, said skin-attaching surface comprising an adhesive for adhering to the skin of the being, said skin-attaching surface having a periphery larger than the periphery of said rigid or semi-rigid base; and said base-attaching surface having a central region and a peripheral edge and wherein said base-attaching surface is coupled to said rigid or semi-rigid base at discrete adhesive locations but is uncoupled to said rigid or semi-rigid base at its central region and at its peripheral edge, thereby minimizing stress omnidirectionally on the skin of the being and reducing the chance of premature detachment from the skin of the being.

14. An attachment system for reliably attaching a device to the skin of a being, and wherein the device includes a rigid or semi-rigid base having a periphery, said system comprising:

a member having viscoelastic properties approaching that of the skin of the being, a skin-attaching surface and a base-attaching surface, said skin-attaching surface comprising an adhesive for adhering to the skin of the being, said skin-attaching surface having a periphery larger than the periphery of said rigid or semi-rigid base; and said base-attaching surface having a central region and a peripheral edge and wherein said base-attaching surface is coupled to said rigid or semi-rigid base at discrete adhesive locations but is uncoupled to said rigid or semi-rigid base at its central region and at its peripheral edge, thereby minimizing stress omnidirectionally on the skin of the being and reducing the chance of premature detachment from the skin of the being.

15. The attachment system of claim 14 wherein one portion of said peripheral edge is coupled to said rigid or semi-rigid base.

16. The attachment system of claim 15 wherein said one portion forms an extension of one of said discrete adhesive locations.

* * * * *